United States Patent
Robinson et al.

(10) Patent No.: US 10,232,416 B1
(45) Date of Patent: Mar. 19, 2019

(54) CORRUGATED AND SLOTTED INJECTION SYSTEM AND METHOD OF USE

(71) Applicants: Lance I. Robinson, Parrish, FL (US); Erik R. Piatt, Lantana, TX (US)

(72) Inventors: Lance I. Robinson, Parrish, FL (US); Erik R. Piatt, Lantana, TX (US)

(73) Assignee: En Rx Chemical, Inc., Argyle, TX (US)

( * ) Notice: Subject to any disclaimer, the term of this patent is extended or adjusted under 35 U.S.C. 154(b) by 388 days.

(21) Appl. No.: 15/066,811

(22) Filed: Mar. 10, 2016

Related U.S. Application Data

(60) Provisional application No. 62/130,988, filed on Mar. 10, 2015.

(51) Int. Cl.
| | | |
|---|---|---|
| *E03F 1/00* | (2006.01) | |
| *B09C 1/00* | (2006.01) | |
| *B09C 1/02* | (2006.01) | |
| *B09C 1/08* | (2006.01) | |
| *C02F 1/72* | (2006.01) | |
| *C02F 3/34* | (2006.01) | |
| *G01N 33/24* | (2006.01) | |
| *C02F 103/06* | (2006.01) | |

(52) U.S. Cl.
CPC ............ *B09C 1/002* (2013.01); *B09C 1/02* (2013.01); *B09C 1/08* (2013.01); *C02F 1/72* (2013.01); *C02F 3/34* (2013.01); *G01N 33/24* (2013.01); *C02F 2103/06* (2013.01)

(58) Field of Classification Search
CPC ... B09C 1/002; B09C 1/02; B09C 1/08; C02F 2103/06
USPC .......................................... 405/128.25, 128.3
See application file for complete search history.

(56) References Cited

U.S. PATENT DOCUMENTS

| | | | |
|---|---|---|---|
| 4,163,619 A | 8/1979 | Fales | |
| 4,582,611 A | 4/1986 | Wang | |
| 4,824,287 A * | 4/1989 | Tracy | E03F 1/002 210/170.08 |

(Continued)

FOREIGN PATENT DOCUMENTS

CN   103920703 A   7/2014

OTHER PUBLICATIONS

Al-Awadhi, et al., Comparison of the potential of coastal materials loaded with bacteria for bioremediating oil sea water in batch culture. Microbiol Res. 2002;157(4):331-6.

(Continued)

*Primary Examiner* — Tara Mayo-Pinnock
(74) *Attorney, Agent, or Firm* — Nicholas Pfeifer; Smith & Hopen, P. A.

(57) ABSTRACT

A device and method for collecting liquid from an underground source or remediating an environmental contaminant from soil or aquifers. The device includes injection tubing having one or more holes, disposed within a corrugated conduit and sieve. An injection channel is provided on the corrugated conduit allowing liquid to flow around the injection system. The injection system can be used in vertical or horizontal well settings. The device is inserted into contaminated soil or an aquifer, and a remediation composition is injected into the soil or aquifer using the injection tubing of the device. One or more of the devices are placed into a well bore, with multiple devices allowing for adaptive, directional injection of the remediation composition.

24 Claims, 7 Drawing Sheets

(56) References Cited

U.S. PATENT DOCUMENTS

| | | | |
|---|---|---|---|
| 6,027,284 A | 2/2000 | Prasher et al. | |
| 6,073,659 A | 6/2000 | Lange | |
| 6,312,190 B1 | 11/2001 | Goughnour | |
| 6,364,572 B1 | 4/2002 | Hudgins et al. | |
| 6,375,388 B1 * | 4/2002 | Zoeller | E03F 1/003 405/43 |
| 6,749,368 B2 | 6/2004 | Ankeny et al. | |
| 6,846,130 B2 | 1/2005 | Goughnour | |
| 6,978,688 B2 | 12/2005 | Engebretson | |
| 7,004,249 B2 | 2/2006 | Lohbeck | |
| 7,615,156 B2 | 11/2009 | Lenger et al. | |
| 8,210,773 B2 | 7/2012 | Swearingen et al. | |
| 2003/0069142 A1 | 4/2003 | Beal | |
| 2010/0178111 A1 * | 7/2010 | Samara | E02B 11/005 405/43 |

OTHER PUBLICATIONS

Sorkoh, et al., Self-cleaning of the Gulf. Nature. Sep. 10, 1992;359(6391):109.

Mahmoud, et al., A microbiological study of the self-cleaning potential of oily Arabian gulf coasts. Environ Sci Pollut Res Int. Feb. 2010;17(2):383-91.

Koerner, Robert M. et al. Leachate Clogging Assessment of Geotextile and Soiul Landfill Filters. US Environmental Protection Agency, 1995.

Construction Dewatering. Environmental Remediation, GroundWater Treatment & Technology, LLC (GWTT). http://www.gwttllc.com/103-services/construction-dewatering. Accessed on Jan. 15, 2016.

Mechanical translation of foreign reference CN103920703A published Jul. 16, 2014 in the name of Jinan Runtu Agricultural Science & Technology Co. Ltd.

\* cited by examiner

CORRUGATED AND SLOTTED INJECTION SYSTEM AND METHOD OF USE

FIELD OF INVENTION

This invention relates to remediation injection systems for in situ remediation of contaminated soil and/or ground water. More specifically, the invention provides a novel system having a slotted corrugated device for removing liquids and/or injecting chemicals and/or biological material into soil or water using for remediation of contaminated soil and/or ground water.

BACKGROUND OF THE INVENTION

Hazardous waste site cleanup is a major environmental concern, with contaminants at many sites posing an immediate environmental concern. Typically, these hazardous waste sites were created by the dumping of hazardous chemicals in inadequately designed dump pits or sites, such as bulk disposal or disposal in leaking or non-corrosion resistant containers. The chemicals at these sites accordingly seep into the underlying soils and into underlying aquifers. The movement of the contaminants within the soil and aquifers has resulted in large the contaminated areas, well beyond the actual dump site.

One method of decontaminating the hazardous waste sites was to completely remove the contaminated soil by excavation, followed by treatment of the removed soil at a processing facility or transport of the soil to another landfill site from which the spread of contaminants was more easily controlled. However, this method is very expensive and time consuming. Moreover, transporting the contaminated soil from one site to another only postpones the eventual treatment.

Another method for mitigating ground water contamination has been fluid removal. In fluid removal systems both drains and wells have been used. Typically, the use of drains involved excavating a pit located toward the downstream end of the contaminant plume. Prior conduit systems have been used for injection or removal of fluids. For example, Wang (U.S. Pat. No. 4,582,611) describes a corrugated drain having a porous filter. Variations use openings in the piping to provide openings for fluid transfer through the piping, as seen in Goughnour (U.S. Pat. No. 6,846,130) and Fales (U.S. Pat. No. 4,163,619). Beal (U.S. application Ser. No. 09/974,726) discloses a device comprising a tube containing baffles, which injects an oxidant to remediate a water borne contaminant as it flows through the device. Similarly, Swearingen, et al. (U.S. Pat. No. 8,210,773) uses piping systems to inject oxidant with the goal of removing pollutants from soil.

However, these drain systems have limited application to shallow plumes and in low permeability soils. Since drains are generally exposed to the surface, this remediation method is not desirable in flood-prone areas. Moreover, removal of contaminants with drain systems is often slow, commonly requiring many years to reduce the contaminants to an environmentally acceptable concentration.

Other systems for remediating contamination include conversion of landfills into bioreactors. For example, Hudgins, et al. (U.S. Pat. No. 6,364,572) provides aeration pipes that inject oxygen or ambient air into the landfill and leachate collection pipes that remove liquid forming in the landfill to provide an improved growth environment for microbes in the landfill, allowing for bio-degradation of contaminants. Similarly, Ankeny, et al. (U.S. Pat. No. 6,749,368) provides aeration pipes installed above a landfill, for injection of air into the soil and monitoring and extraction of contaminants.

Currently the industry (horizontal drilling) drill long continuous wells (several hundred to thousands of feet long) to do environmental work. The main drawback is the singularity of traditional wells.

However, these systems provide a simple conduit for direct pumping of fluid into the soil or removal of fluid from the soil. What is needed is a means to direct remediation materials to specific zones on subsurface structures to effectuate directed decontamination of a soil or other matrix.

SUMMARY OF THE INVENTION

In contrast to the known methods for removing contaminants from hazardous waste sites, the instant invention provides a method of soil decontamination and cleanup of groundwater which is less expensive, which gives higher reliability, and which produces the desired results in a significantly more timely manner.

The injection system comprises a sieve having an upper end and a lower end and an interior lumen. The sieve is made of flexible or semi-flexible material, such as geotextile sock, wire mesh, or stainless steel screen. Exemplary geotextile socks include geotextile polyethylene, polypropylene, high density polyethylene, fiberglass, and combinations thereof. A corrugated conduit is provided in the interior lumen of the sieve. The corrugation ridges of the conduit run perpendicular to the longest axis of the corrugated conduit. The corrugated conduit also has at least one injection channel running parallel to the longitudinal axis of the corrugated conduit, and formed from partial removal of the ridges of the corrugated conduit. For example, partial removal of corrugated conduit wall, of from $\frac{1}{4}$ to $\frac{1}{2}$ the overall thickness of the corrugated conduit wall, along a straight line forms a channel. Optionally, the partial removal is at a thicknesses of $\frac{1}{4}$ $\frac{1}{3}$, $\frac{3}{8}$, $\frac{1}{2}$ the overall thickness of the corrugated conduit wall The channel is continuous along the length of the corrugated conduit. The corrugated conduit is HDPE, LDPE, HDPE/LDPE (high-density polyethylene, low-density polyethylene), steel, rubber, or polyvinyl chloride (PVC) or plastic. Examples of plastics include polyester, polyethylene terephthalate, polyethylene, polyvinylidene chloride, polypropylene, polystyrene, high impact polystyrene, polyamides, acrylonitrile butadiene styrene, polyethylene/acrylonitrile butadiene styrene, polycarbonate/acrylonitrile butadiene styrene, polyurethane, polycarbonate, phenolics, such as Bakelite, polyetheretherketone, polyimide, and polylactic acid, and other plastics.

An injection tubing is disposed in the interior lumen of the corrugated conduit, and has at least one injection hole disposed in the tubing wall. The injection tubing is made of HDPE/LDPE, KYNAR (a polyvinylidene fluoride (PVDF) resin), flexible steel, rubber lines, PVC, or other plastic, such as those discussed in the application. The injection tubing has openings disposed along the length of the tubing. The openings can be circular and formed from drilling, die cutting, transverse slotted tubing, longitudinal slotted tubing, or variable slot design tubing. An injection cap is used on the matrix end of the injection tube, thereby preventing free flow of materials through the matrix end of the injector. The injection cap is formed of plastic, metal, rubber, or silicon. Rubber that is useful for the injector cap includes latex (natural) rubber, isoprene rubber, ethylene propylene diene rubber, nitrile rubber (copolymer of butadiene and acrylonitrile), isobutylene isoprene butyl rubber, bromo isobutylene isoprene rubber, chloro-isobutylene isoprene rubber, styrene butadiene rubber, silicone rubber, isobutylene isoprene rubber, polyisobutylene rubber, polybutadiene rubber, polychloroprene rubber, acrylonitrile butadiene rubber, ethylene-acrylate rubber, polyester urethane rubber, polyether urethane rubber, polyacrylate rubber, chlorosulphonated polyethylene rubber, ethylene propylene rubber, ethylene propylene diene monomer rubber, perfluorocarbon rubber, epichlorohydrin rubber, fluoro silicone rubber, fluorocarbon rubber, hydrogenated nitrile butadiene rubber, styrene butadiene block copolymer rubber, thermoplastic polyether-ester rubber, acrylonitrile butadiene carboxy monomer rubber, vinyl methyl silicone rubber, polysiloxane rubber, styrene ethylene rubber, and butylene styrene copolymer rubber. Specific embodiments are envisioned constructed of plastic. Some examples of useful plastics include polyethylene, polypropylene, polyethylene terephthalate, polyvinylchloride, polyvinylidenechloride, polycarbonate, polyurethane, polyamide, polytetrafluoroethylene, polyvinylacetate, acrylonitrile butadiene styrene (ABS), high impact polystyrene (HIPS), acrylic (PMMA), cellulose acetate, cyclic olefin copolymer (COC), ethylene-vinyl acetate (EVA), ethylene vinyl alcohol (EVOH), polyvinylfluoride (PVF), polyvinylidene fluoride (PVDF), polytetrafluoroethylene (PTFE), polychlorotrifluoroethylene (PCTFE), fluorinated ethylene-propylene (FEP), perfluoroalkoxy polymer (PFA), polyethylenechlorotrifluoroethylene (ECTFE), polyethylenetetrafluoroethylene (ETFE), perfluoropolyether (PCPE), acrylic/PVC polymer, aromatic polyester polymers (liquid crystal polymer), polyoxymethylene (acetal), polyamide (PA, nylon), polyamide-imide (PAI), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoate (PHA), polyketone (PK), polyester, polyethylene (PE), polyetheretherketone (PEEK), polyetherimide (PEI), polyethersulfone (PES), chlorinated polyethylene (CPE), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (FIT), polyurethane (PU), polyvinyl acetate (PVA), polyvinyl chloride (PVC), polyvinylidene chloride (PVDC), styrene-acrylonitrile (SAN).

The injection hole is about 3/32 inches in diameter. For example, the injection tube can be 1/16 (2/32), 5/64, 3/32, 7/64, or 1/8 (4/32) inches in diameter. In some variations, the injection holes are disposed at between 1 hole per foot and 5 holes per foot. For example, the holes may be disposed at 1 hole per foot, 1.25 holes per foot (1 hole every 0.8 feet), 1.5 holes per foot (1 hole every 0.67 feet), 1.75 holes per foot (1 hole every 0.57 feet), 2 holes per foot (1 hole every 0.5 feet), 2.25 holes per foot (1 hole every 0.44 feet), 2.5 holes per foot (1 hole every 0.4 feet), 2.75 holes per foot (1 hole every 0.36 feet), 3 holes per foot (1 hole every 0.33 feet), 3.25 holes per foot (1 hole every 0.31 feet), 3.5 holes per foot (1 hole every 0.29 feet), 3.75 holes per foot (1 hole every 0.27 feet), 4 holes per foot (1 hole every 0.25 feet), 4.25 holes per foot (1 hole every 0.24 feet), 4.5 holes per foot (1 hole every 0.22 feet), 4.75 holes per foot (1 hole every 0.21 feet), or 5 holes per foot (1 hole every 0.2 feet). Some variations provide that the injection holes are equally spaced along the distance of the injection tubing. Alternatively, the injection tube uses slots. In certain embodiments, the slots are about 4 inches in length and are spaced about 18 inches apart. For example, the slots can be 3.4 inches in length, 3.5 inches in length, 3.6 inches in length, 3.7 inches in length, 3.8 inches in length, 3.9 inches in length, 4 inches in length, 4.1 inches in length, 4.2 inches in length, 4.3 inches in length, 4.4 inches in length, 4.5 inches in length, or 4.6 inches in length. The slots can be spaced 15.3 inches apart, 15.4 inches apart, 15.5 inches apart, 15.6 inches apart, 15.7 inches apart, 15.8 inches apart, 15.9 inches apart, 16 inches apart, 16.1 inches apart, 16.2 inches apart, 16.3 inches apart, 16.4 inches apart, 16.5 inches apart, 16.6 inches apart, 16.7 inches apart, 16.8 inches apart, 16.9 inches apart, 17 inches apart, 17.1 inches apart, 17.2 inches apart, 17.3 inches apart, 17.4 inches apart, 17.5 inches apart, 17.6 inches apart, 17.7 inches apart, 17.8 inches apart, 17.9 inches apart, 18 inches apart, 18.1 inches apart, 18.2 inches apart, 18.3 inches apart, 18.4 inches apart, 18.5 inches apart, 18.6 inches apart, 18.7 inches apart, 18.8 inches apart, 18.9 inches apart, 19 inches apart, 19.25 inches apart, 19.5 inches apart, 19.75 inches apart, 20 inches apart, 20.25 inches apart, 20.5 inches apart, or 20.7 inches apart. In specific variations, the slots are 4 inches and spaced 18 inches apart. In advantageous variations, the slots in the injection tube are equally spaced along the distance of the injection tubing.

Strap or tie wraps are optionally used to secure the sieve to the ends of the system, such as the surface end and matrix end of the injection tubing. Exemplary materials include steel, metal or plastic, such as the plastics discussed previously.

The injection system has at least one continuous injection channel and injection/extraction points along the length of the system, providing for injection or extraction over the entire length of the device. The injection systems disclosed herein can be used independently or in a group, such as a bundle of systems disposed in adjacent wells. For example, a series of 6 wells use six injection systems, allowing for control of 6 independent well screen (socked conduit) sections adding control to a formerly uncontrolled environmental situation. Alternatively, one or more bore holes are provided, with each bore hole containing a plurality of injection systems. For example, wand without limiting the scope of the invention, each bore can include 3 injection systems, 4 injection systems, 5 injection systems, 6 injection systems, 7 injection systems, 8 injection systems, 9 injection systems, 10 injection systems, or 11 injection systems.

A method for removing hazardous chemicals from contaminated soil or aquifers is also provided. The method includes the steps of inserting at least one of the injection systems, described above, into a bore well. The site is then remediated by injecting a remediator, suspended in a liquid carrier, into the soil or other matrix and allowing the remediator to degrade the contaminant. Alternatively, the site is remediated by applying negative pressure to the injection system or allowing hyperbaric pressure to drive the contaminant toward the soil or matrix surface and removing the contaminant once it reaches the surface.

Where a remediator is injected into the soil or matrix, the remediator is optionally a chemical oxidant (ChemOx) or a biological remediator. Useful chemical oxidants are oxidizing agents, such as a permanganate, peroxide, or persulfate. Specific examples include potassium permanganate and sodium permanganate. Biological remediators include microbes, such as *Deniococcus radiodurans, Burkholderia xenovorans, Rhodococcus* sp. strain RHA1, *Aromatoleum aromaticum* strain EbN 1 *Geobacter metallireducens, Dehalococcoides ethenogenes* strain 195, *Dehalococcoides* sp. strain CBDB1, *Desulfitobacterium hafniense* strain Y51,

*Acinetobacter calcoaceticus, Micrococcus* sp. (Al-Awadhi, et al., Comparison of the potential of coastal materials loaded with bacteria for bioremediating oil sea water in batch culture. Microbiol Res. 2002; 157(4):331-6) and naturally-occurring species, such as blue-green bacteria found in the Arabian Gulf (Sorkoh, et al., Self-cleaning of the Gulf. Nature. 1992 Sep. 10; 359(6391):109; Mahmoud, et al., A microbiological study of the self-cleaning potential of oily Arabian gulf coasts. Environ Sci Pollut Res Int. 2010 February; 17(2):383-91). In some variations, the bacteria can be genetically engineered microorganisms containing genes to allow or improve degradation of contaminants. The remediator is optionally suspended in a water carrier.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
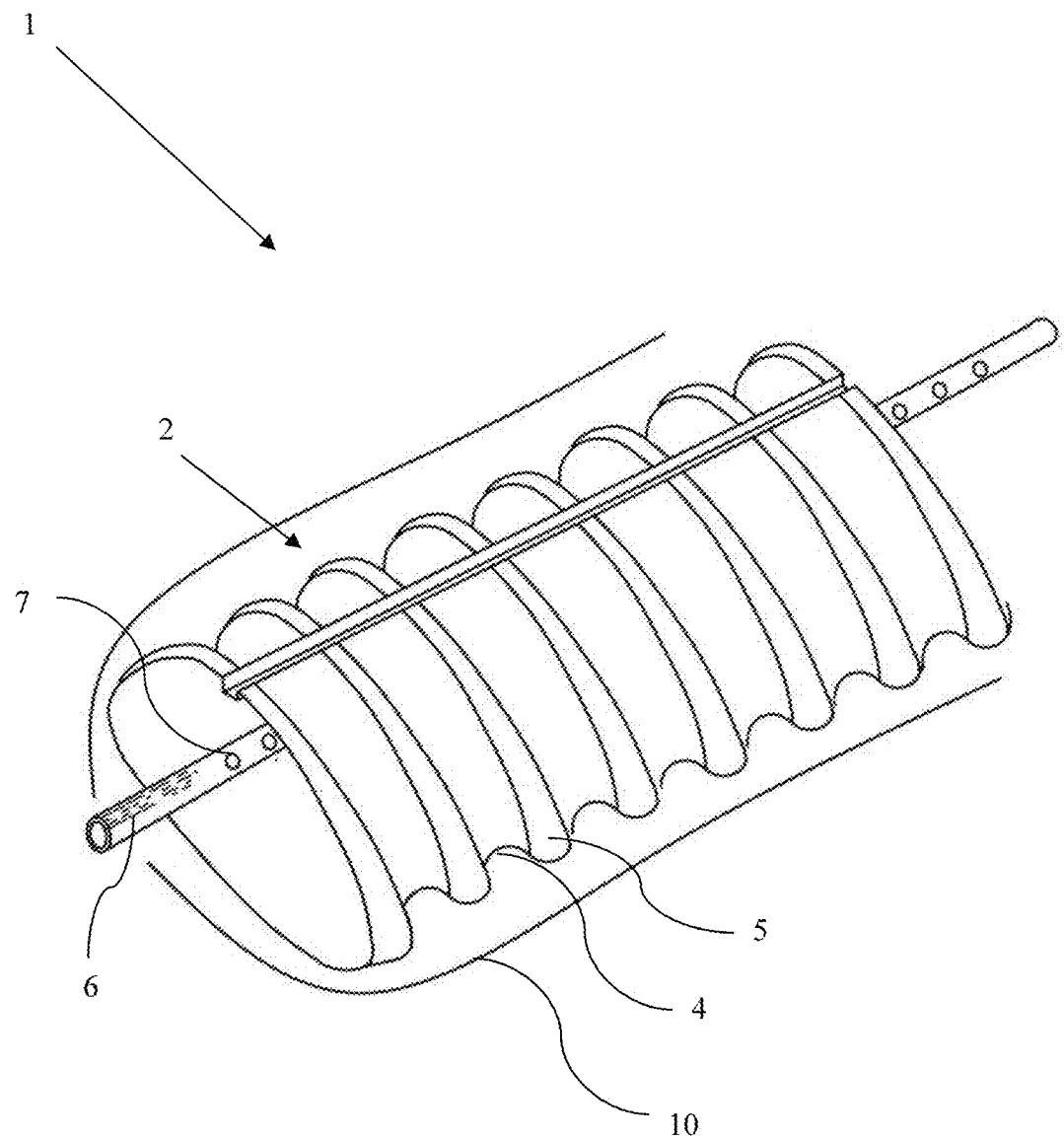
FIG. 1 is an isometric cut-away view of the injection system, showing the injection tubing within the corrugated conduit and encased in the sieve.

The disclosed device is an injection system used in environmental well applications. Advantageously, the injection system can be used for both extraction of fluid and injection of fluids. For example, injection system has applications in extraction of groundwater or vapor that may be contaminated, or for injection of chemicals, elements or remedial materials that aide in environmental restoration.

The device is used as an environmental well. It may function for extraction of fluid, injection of fluids, or both extraction and injection; ie. extraction of groundwater or vapor that may be contaminated. Or the injection of products, chemicals, elements or anything that aide in environmental restoration.

As used herein, the singular forms "a," "an" and "the" include plural referents unless the context clearly dictates otherwise. Thus, for example, reference to "a biological material" includes a mixture of two or more materials and the like.

As used herein, "about" means approximately and is understood to refer to a numerical value or range of +15% of the numerical. Moreover, all numerical ranges herein should be understood to include all integer, whole or fractions, within the range.

As used herein "matrix" means a material containing an environmental contaminant. Examples of substrates include soil, clay, and water sources, such as ponds and lakes.

As used herein "tube" or "pipe" refers to any compressible or non-compressible cylindrical structure having a hollow interior lumen and provides a conduits or passageway for fluids.

As used herein "corrugation" or "corrugated" refers to a structure having wavy or ridged surface.

As used herein "chemical remediator" is any compound that reacts with and degrades a contaminant, such as a hydrocarbon. Chemical remediators can include oxidizing chemicals or reducing chemicals.

As used herein "oxidizing chemical" means a chemical that possesses the capacity to undergo a reaction in which electrons are obtained from another material identified as an environmental contaminant.

As used herein "reducing chemical" means a chemical that possesses the capacity to undergo a reaction in which electrons are lost to another material identified as an environmental contaminant.

As used herein "biological remediator" is any microbe having a natural or genetically engineered ability to degrade, metabolize, or otherwise remediate an environmental contaminant a contaminant, such as a hydrocarbon.

As used herein the terms "microorganism" and "microbe" refer to tiny organisms. Most microorganisms and microbes are unicellular, although some multicellular organisms are microscopic, while some unicellular protists and bacteria (e.g., *T. namibiensis*) called are visible to the naked eye. Microorganisms and microbes include, but are not limited to, bacteria, fungi, archaea and protists, microscopic plants, and animals (e.g., plankton, the planarian, the amoeba) and the like.

Contaminant remediation requires identification of a contaminated matrix, i.e. location of the contaminant, and degradation or removal of the contaminant. However, as most remediators are not without side effects, it is preferable to have focused contaminant treatment, directed to the contaminant. However, previous systems indiscriminately undergo treatment—whether through indirect injection of remediator or generalized removal of contaminated fluids—resulting in chemicals or biologicals in uncontaminated soil, and higher required amounts of chemicals or biologicals. As such, a remediation composition delivery system is provided that allows for directed injection of a chemical or biological agent into the soil and/or groundwater to treat contamination. Advantageously, the system can also be used for detection of subsurface contaminants.

Example 1

Remediation of soil or groundwater contamination is accomplished through introduction of a chemical or biological agent to the contaminated material, followed by degradation of the contaminant. Accordingly, remediation systems require a means to inject the chemical or biological agent as well as a means to monitor the degradation of the contaminant. To address both needs, injection system 1 is comprised of injection tubing 6 disposed in the interior lumen of corrugated conduit 2, which is encased in sieve 10, as seen in FIG. 1.

Injection tubing 6 is formed from high density polyethylene (HDPE) tubing. A plurality of holes 7 are drilled into injection tubing 6. The holes have a diameter of about 3/32 inches. While 3/32 inches is used, the dimensions may vary. The placement and number of holes varies based on the desired liquid flow characteristics and length of the tubing, i.e. depth of insertion in diameter. For example, where a water flow of 0.5 gpm is desired, 20 holes are drilled into a 20-foot long injection tubing, i.e. one hole per foot. For water flow of 1 gpm, holes 7 are disposed half as far, i.e. every ½ foot or 40 holes for a 20-foot long injection tubing, allowing the liquid flow rate to be scalable. Preferably, the holes are evenly spaced. Further, the number of holes varies based on the length of the injection tubing, such as a length of 3-30 ft will likely have 3 holes for a 3-foot long injection tube having a 0.5 gpm flow rate to 30 holes for a 30-foot long injection tube having a 0.5 gpm flow rate.

Figure 2:
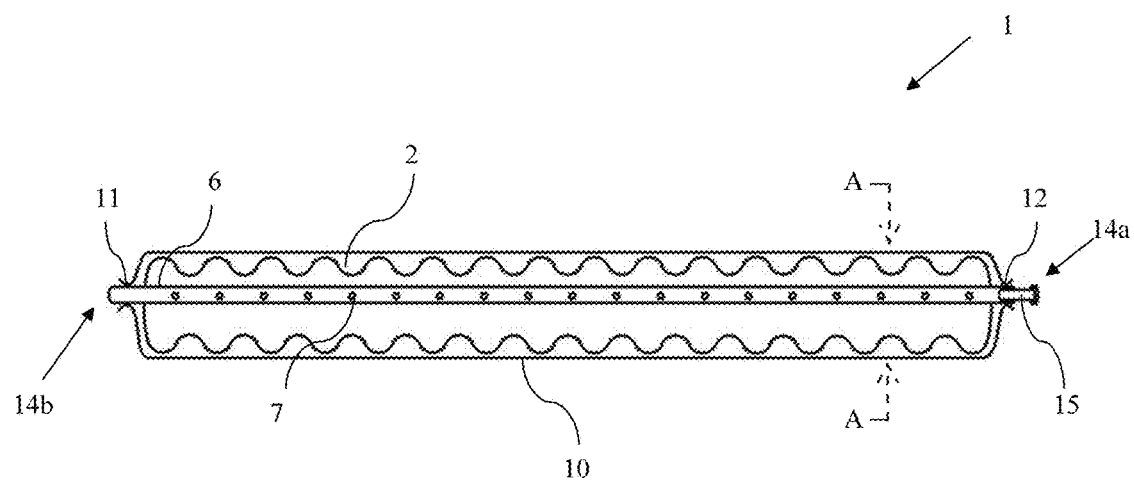
FIG. 2 is a longitudinal cross section of the injection system showing the corrugated conduit and injection tubing.

Injection cap 15 is disposed on the matrix end 14a of injection tubing 6, i.e. the end distal to the surface, or surface end 14b, as seen in FIG. 2. Preferably, injection cap is adapted to affix to an injection system or injection pump. The injection cap is formed of plastic, such as polyethylene. Useful examples of an injection system or injection pump include positive displacement pumps such as diaphragm pumps (air operated or electric), screw pumps, metering pumps (electric or magnetic/solenoid), pistons pumps or centrifugal pumps, jet pumps, and electric diaphragm pumps.

Figure 3:
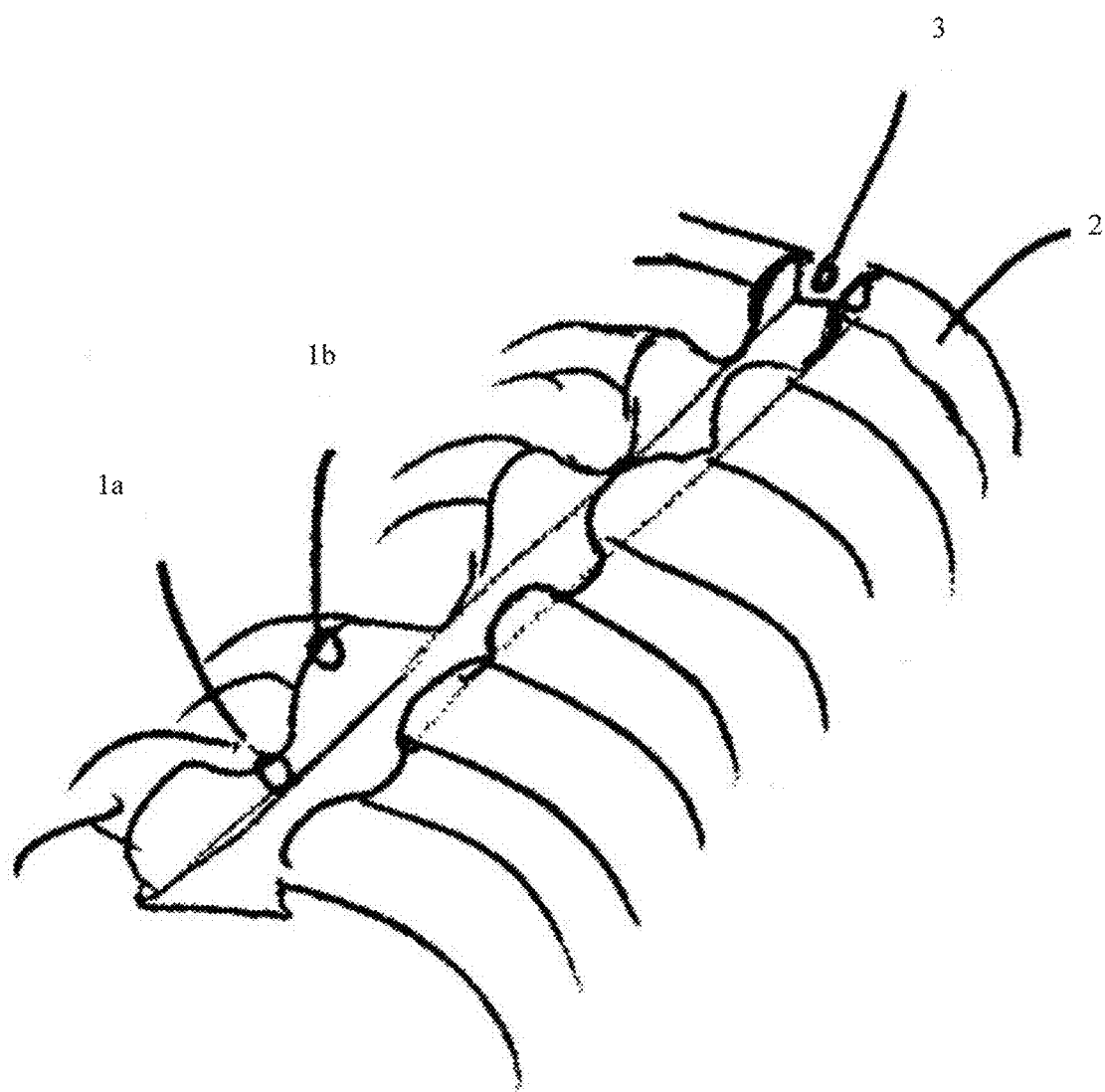
FIG. 3 is an isometric view of the corrugated tubing, showing the injection channel.

Corrugated conduit 2 comprises a plurality of corrugated ridges formed of trough 4 and peak 5 disposed perpendicular to the axis of corrugated conduit 2, as seen in FIG. 1. The corrugated conduit is formed of low density polyethylene (LDPE) tubing. Injection channel 3 runs parallel to the axis of corrugated conduit 1, as seen in FIG. 2. Injection channel 3 is formed from partial removal of the corrugated conduit, i.e. external rib 1b, while retaining the remainder of the corrugated conduit, i.e. internal rib 1a. As an example, a circular saw can be used to remove external rib 1b while retaining internal rib 1a, and allow the conduit's internal rib to leak the fluid uniformly over the body length, as seen in FIG. 3. The remaining portions of the external rib after formation of injection channel 3 provide channels that allow fluid to travel around the body of injection system 1.

Sieve 4 is the outermost portion of injection system 1 and encases the aforementioned elements. The sieve is a geotextile sock, formed of polyester. The ends of sieve 4 are fixed to injection tubing 6 at matrix end 14a via second sieve connector 12 and at surface end 14b via first sieve connector 11. First sieve connector 11 and second sieve connector 12 can be any fastener known in the art for fixing to tubular structures. Examples of fasteners include tie wraps for the sieve at the lower-most section and steel, plastic, or metal bands or tie wraps around the sieve and tubing at the upper-most section.

Figure 4:
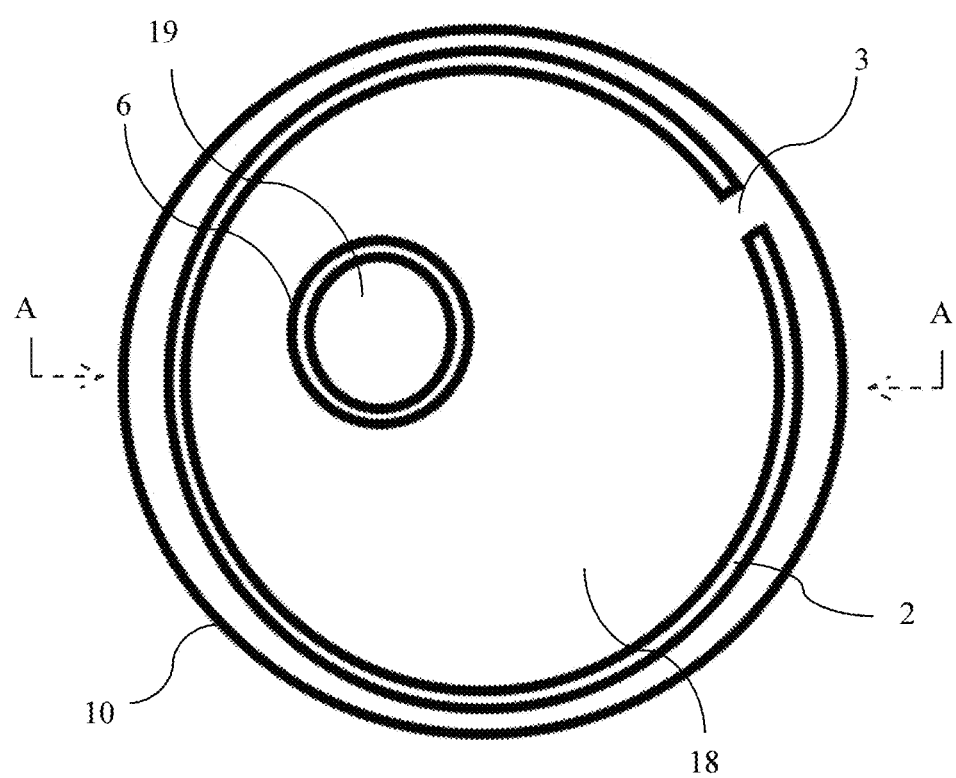
FIG. 4 is a transverse cross section injection system, at position A-A of FIG. 2, showing the corrugated conduit, injection channel, injection tubing, and sieve.

Injection tubing 6 is inserted into corrugated conduit lumen 18, thereby disposing injection tubing 6 within corrugated conduit 1. The corrugated conduit with injection tubing is then inserted into sieve 4, seen in FIG. 4. The rib of corrugated conduit 1 provides a pocket between corrugated conduit 1 and sieve 4, allowing the fluid to flow around the body exterior of corrugated conduit, while the soil is supported by sieve 4.

Example 2

Figure 5:
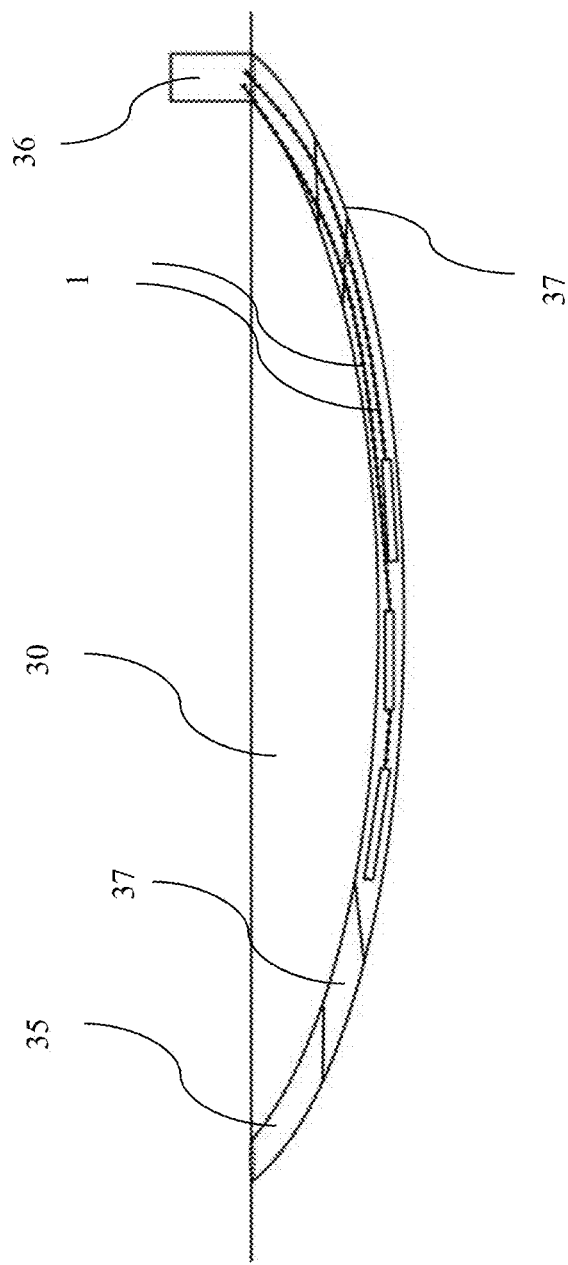
FIG. 5 is an illustration showing installation of the devices in a bore hole.

The injection system is installed into a soil substrate to remediate a subsurface contaminant. Bore hole 35 is drilled into soil substrate 30 using vertical or horizontal drilling techniques methods known in the art, such as horizontal directional drilling (HDD), cable tool drilling, auger drilling, rotary drilling, jet drilling, and variants therein, such as reverse circulation rotary drilling, mud rotary drilling, and air rotary drilling. Drill holes size can be varied as well as drill hole spacing. Injection system 1 is installed into bore hole 35 for collection of liquid or injection of materials, such that the longitudinal axis of injection system 1 aligns parallel to the longitudinal axis of bore hole 35, as seen in FIG. 5. In specific embodiments, up to eleven independent injection systems are inserted into a single 4" bore hole. Advantageously, injection system 1 is optionally installed within a strata (lithologic or geologic) or congruent to the strata. Locking protective riser 36 is installed over bore hole 35 head. Various strata in bore hole 35 are isolated using bentonite seal 37. Where a horizontal directional drilling bore hole is used, bentonite seal 37 is placed on the bore hole head side and bore hole exit side of the hole. Advantageously, the injection system provides flexibility (bend and flex) not available with other slotted well screens. During installation into a horizontal well, device flexibility is useful for installation.

Example 3

A contamination site in south Florida, currently in use and containing buildings required contamination detection and analysis. A common issue for contamination detection and analysis is the existence of a building or structure impeding access to contaminated soil. In many instances, the building or structure lies above the source of contamination, where soil sampling is most advantageous. Data gaps typically cause significant problems in contamination sampling, leading to prolonged remediation and higher costs. Even though assessment is well recognized, and high resolution site characterization (HRSC) has made great advances in more complete more accurate assessments, this problem has not been addressed by known sampling, detection, and analysis methodology.

Figure 6:
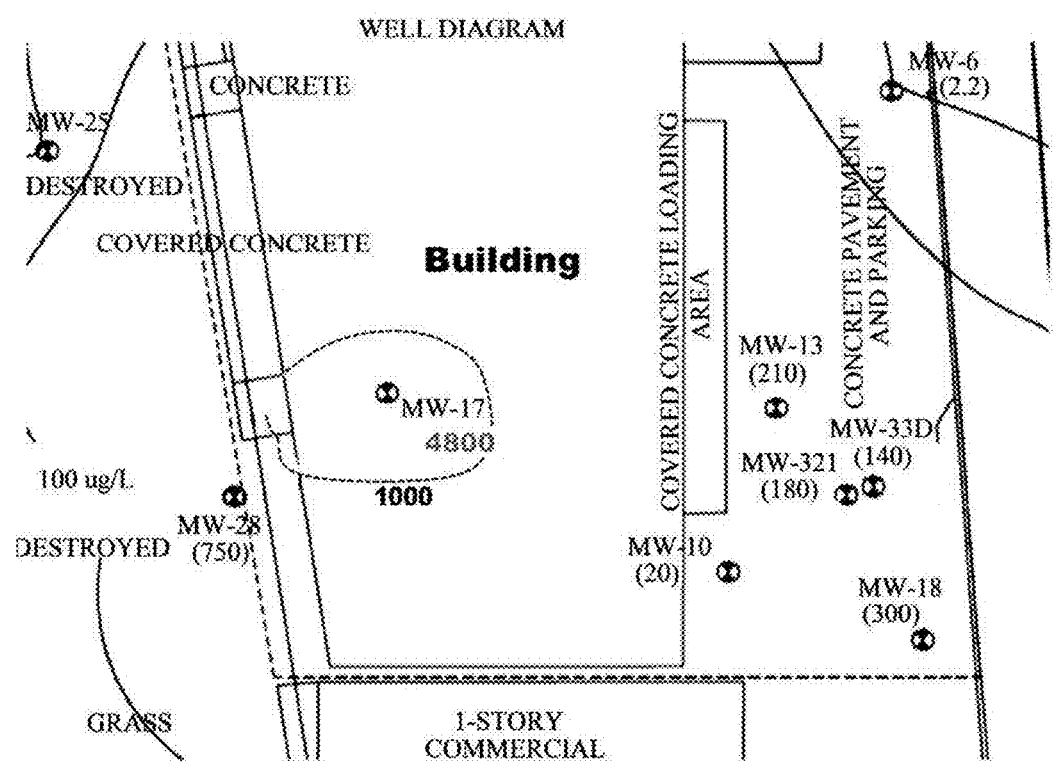
FIG. 6 is an illustration of the initial assessment of a test site, prior to installation of the injection system.

The south Florida site contained an active i.e. in-use, 80 foot wide building with an assortment of equipment and small hallways, as seen in FIG. 6. Silty sand and sandy clays typical of Florida reside in the top 15 ft. The lithology transitions to a clay confining layer at 15 to 17 ft below land surface (bls). Sampling systems would lead to a very costly and disruptive interior assessment, preventing use of HRSC or other traditional sampling systems. Initial assessment of the contamination suggested a high contamination concentration at the southwest portion of the building, of around 4800 ppb. The present invention was installed at the site, including one vertical bore well installed inside the building (MW-17) and four horizontal bore wells outside the building.

Horizontal bore holes were formed using horizontal directional drilling (HDD), and a plurality of injection tube 1 were installed into each bore hole 35. This allowed for the bore holes to be drilled from outside the building, but precisely located under the building, which was required to obtain accurate data on the site contamination. The HDD bores were advanced to install a total of 26 well segments under the building in 7 days.

Figure 7:
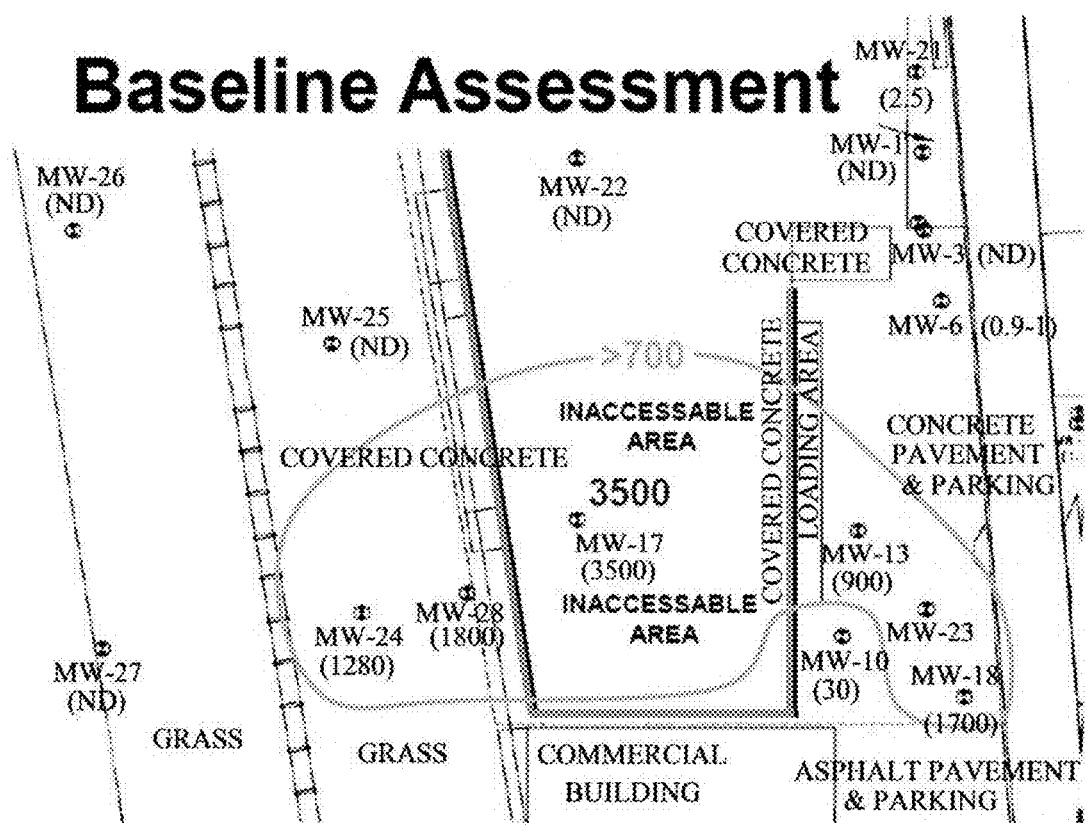
FIG. 7 is an illustration of the final assessment of the test site shown in FIG. 6, showing initial assessment from the injection system.

The wells were approximately 25 ft on center. However, the horizontal spacing can be adjusted as required for the site, which would be within the skill of one in the art. For example, wells can be installed 10 ft on center to allow increased precision similar to HRSC data collection. The wells were installed directly on top of the clay confining layer at the site. It was known that the solvents sank down to this layer and the most concentrated sample results would be collected from this depth (approximately 15 ft bls). Five monitoring wells, screened from 5-15, characterize the plume, MW-17, MW-28, MW-13, MW32I, and MW-18, as seen in FIG. 7. These wells were developed and sampled after the development water cleared and in situ parameters stabilized. Initial assessment using the injection devices showed a concentration at the southwest corner at 3500 ppb. The multi-channel well installation of the invention allowed the sampling to provide a clearer location for the contaminant source and a more accurate representation of the plume. This permitted for formation of a directed, specific remediation plan to move forward. The provided data has the clarity and spacing similar to HRSC tools. Unlike most HRSC tools, these wells can be resampled again and again. This allows for re-monitoring of the site conditions, instead of having to recomplete a HRSC event.

Sampling indicated that the most impacted well, MW-1700, had a concentration of HVOCs of 4,800 ppb. Analysis of the collected data showed the highest levels of HVOCs were focused in a zone under the building, presumably indicating a source of the contaminant, and also provided a reliable estimate of contaminant mass present. Further, the data showed a clear indication of the isocontours of the contaminant plume, as seen in FIG. 7.

Advantageously, the bore holes provide numerous utilities to the site operator. The original intent of the installation at this site was for treatment. The sampling performed after installation provided a detailed description of the contaminant, as described above, and allowed for a directed, specific remediation plan. For example, after review of the data, it was decided to place screens for future treatment, and the locations for the screens determined. Chemical oxidant treatment (ChemOx) was elected for remediation due to the rapidity of contaminant removal. The screens allow for ChemOx treatment at a precise depth, as well as to target specific locales for treatment. However, where quick remediation is not required, treatment can be via bio-remediation or extraction of the groundwater. Injection device 1 permits for the data collection and remediator administration, i.e. injection, using the same device, thus the device is multipurpose. Advantageously, this decreases installation time, costs, and impact on the substrate, such as soil, since the device need be installed only once.

In instances such as this site, not all the wells have to be used for treatment; some can be reserved for sampling only. The installation occurs congruent to the lithology and plume shape. It allows better treatment and less overall drilling. Only one vault is needed per well group minimizing unsightly well pads. Further, installation and use of the inventive device significantly reduced costs.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of remediation injection systems and method for remediating contaminated soil and/or ground water using the same, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. An injection system, comprising:
 a sieve having an upper end and a lower end and an interior lumen, wherein the sieve is made of flexible or semi-flexible material;
 a corrugated conduit disposed in the interior lumen of the sieve,
  wherein the corrugated conduit has a plurality of peaks formed of a plurality of external ribs and troughs formed of a plurality of internal ribs;
  wherein the plurality of peaks and troughs are disposed perpendicular to the longitudinal axis of the corrugated conduit, and wherein the corrugated conduit has an interior lumen;
 at least one injection channel formed on the outer surface of the corrugated conduit and running parallel to the longest axis of the corrugated conduit, wherein the at least one injection channel is formed from removal of the plurality of external ribs of the corrugated conduit;
 an injection tubing disposed in the interior lumen of the corrugated conduit, having a matrix end and a surface end;
 wherein the injection tubing has at least one injection hole disposed in the tubing wall; and
 an injection cap disposed on the matrix end of the injection tubing, thereby restricting injected fluids from exiting the matrix end of the injection tubing.

2. The injection system of claim 1, wherein the sieve is a geotextile sock, wire mesh, or stainless steel screen.

3. The injection system of claim 2, wherein the sieve is a polyester geotextile sock.

4. The injection system of claim 1, wherein the corrugated conduit is high density poly ethylene, low density polyethylene, a composite of high density poly ethylene and low density polyethylene, steel, rubber, or polyvinyl chloride or plastic.

5. The injection system of claim 4, wherein the corrugated conduit is low density polyethylene.

6. The injection system of claim 1, wherein the corrugated conduit has a thickness measured from the peak of the external rib of the corrugated conduit to the trough of the internal rib of the corrugated conduit, and
 wherein the at least one injection channel is formed by partially removing the exterior ¼ to ½ thickness of the external rib.

7. The injection system of claim 1, wherein the at least one injection hole is about 3/32 inches in diameter.

8. The injection system of claim 1, further including a plurality of injection holes, each injection hole being disposed at between 1 hole per foot and 5 holes per foot.

9. The injection system of claim 1, further including a plurality of injection holes, each injection hole being equally spaced along the distance of the injection tubing.

10. The injection system of claim 1, further comprising an injection system or injection pump in fluid communication with the surface end of the injection tubing, where the injection system or injection pump is a positive displacement pump, a diaphragm pumps, a screw pump, a metering pump, a piston, a pump, a centrifugal pump, a jet pump, or an electric diaphragm pump.

11. The injection system of claim 1, wherein the injection tubing is high density poly ethylene, low density polyethylene, a composite of high density poly ethylene and low density polyethylene, a polyvinylidene fluoride resin, flexible steel, rubber lines, polyvinyl chloride, or plastic.

12. The injection system of claim 11, wherein the injection tubing is high density polyethylene tubing.

13. The injection system of claim 1, further comprising a strap or tie wrap disposed on the lower end of the sieve.

14. The injection system of claim 13, wherein the strap or tie wrap is steel, plastic, or metal band.

15. The injection system of claim 1, further comprising a strap or tie wrap disposed on the upper end of the sieve,
   wherein the upper end of the sieve surrounds the injection tubing.

16. The injection system of claim 15, wherein the strap or tie wrap is steel, plastic, or metal band.

17. A method of remediating an environmental contaminant, comprising:
   providing at least one injection system, comprising:
      a sieve having an upper end and a lower end and an interior lumen, wherein the sieve is made of flexible or semi-flexible material;
      a corrugated conduit disposed in the interior lumen of the sieve,
         wherein the corrugated conduit has a plurality of peaks formed of a plurality of external ribs and troughs formed of a plurality of internal ribs;
         wherein the plurality of peaks and troughs are disposed perpendicular to the longitudinal axis of the corrugated conduit, and wherein the corrugated conduit has an interior lumen;
      at least one injection channel formed on the outer surface of the corrugated conduit and running parallel to the longest axis of the corrugated conduit, wherein the at least one injection channel is formed from removal of the plurality of external ribs of the corrugated conduit;
      an injection tubing disposed in the interior lumen of the corrugated conduit, having a matrix end and a surface end;
         wherein the injection tubing has at least one injection hole disposed in the tubing wall;
      an injection cap disposed on the matrix end of the injection tubing;
   providing a vertical or horizontal bore hole;
   inserting the at least one injection system into the bore hole; and
   remediating the contaminant, wherein the remediation is accomplished through remediator injection or contaminant extraction.

18. The method of claim 17, wherein the carrier liquid is water.

19. The method of claim 17, further comprising injecting the carrier and remediator into the soil.

20. The method of claim 17, further comprising providing a plurality of injection systems into a single bore hole.

21. The method of claim 20, wherein up to eleven injection systems are inserted into the single bore hole.

22. The method of claim 17, wherein the negative pressure source is a pump.

23. The method of 17, further including providing a seal on either side of the sieve.

24. A method of collecting data on contaminant concentration and location in a subsurface matrix, comprising:
   providing at least one injection system, comprising:
      a sieve having an upper end and a lower end and an interior lumen, wherein the sieve is made of flexible or semi-flexible material;
      a corrugated conduit disposed in the interior lumen of the sieve,
         wherein the corrugated conduit has a plurality of peaks formed of a plurality of external ribs and troughs formed of a plurality of internal ribs;
         wherein the plurality of peaks and troughs are disposed perpendicular to the longitudinal axis of the corrugated conduit, and wherein the corrugated conduit has an interior lumen;
      at least one injection channel formed on the outer surface of the corrugated conduit and running parallel to the longest axis of the corrugated conduit, wherein the at least one injection channel is formed from removal of the plurality of external ribs of the corrugated conduit;
      an injection tubing disposed in the interior lumen of the corrugated conduit, having a matrix end and a surface end;
         wherein the injection tubing has at least one injection hole disposed in the tubing wall;
      an injection cap disposed on the matrix end of the injection tubing;
   providing a vertical or horizontal bore hole;
   inserting an injection system into the bore hole;
   extracting a sample from the subsurface matrix; and
   subjecting the sample to chemical testing to determine presence and concentration of a contaminant.

\* \* \* \* \*